United States Patent [19]

Hall et al.

[11] Patent Number: 4,629,803

[45] Date of Patent: Dec. 16, 1986

[54] CONTINUOUS PHOSPHORYLATION PROCESS

[75] Inventors: Tawny R. Hall; Harry M. Smith, both of St. Albans, W. Va.

[73] Assignee: FMC Corporation, Philadelphia, Pa.

[21] Appl. No.: 630,143

[22] Filed: Jul. 12, 1984

Related U.S. Application Data

[63] Continuation-in-part of Ser. No. 467,008, Feb. 16, 1983, abandoned.

[51] Int. Cl.$^4$ .............................................. C07F 9/09
[52] U.S. Cl. .................................................... 558/92
[58] Field of Search .......................... 260/974; 558/92

[56] References Cited

U.S. PATENT DOCUMENTS 3,020,303 2/1962 Pianfetti et al. ..................... 260/974
4,421,695 12/1983 Parsons et al. ....................... 260/974

Primary Examiner—Anton H. Sutto
Attorney, Agent, or Firm—Charles C. Fellows; Robert L. Andersen

[57] ABSTRACT

A continuous process for producing alkyl and alkoxy alkyl phosphates in which an alkali metal alkoxide at a temperature at 50° C. or less is continuously fed to a reactor while phosphorus oxychloride is continuously fed to the reactor under ratio control. Part of the contents of the reactor is circulated through a cooling device or apparatus to help maintain optimum reaction temperature. The phosphorus oxychloride ratio is adjusted to maintain proper reaction end point. Crude reaction product is continuously removed from the reactor and quenched with water to remove sodium chloride and stop the reaction.

4 Claims, 1 Drawing Figure

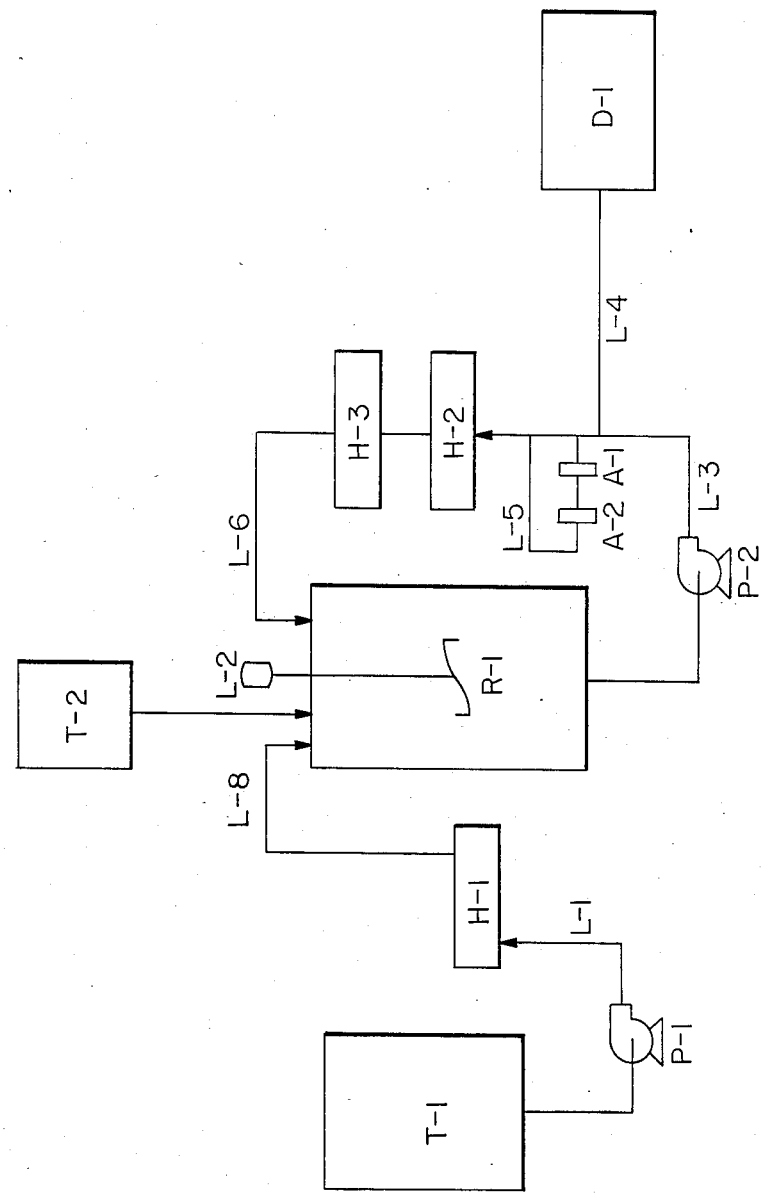

CONTINUOUS PHOSPHORYLATION PROCESS

This application is a continuation-in-part of application Ser. No. 467,008 filed Feb. 16, 1983, now abandoned, of the same title.

This invention relates to a continuous process for producing aliphatic phosphate esters by continuous reaction an alkali metal alkoxide with phosphorus oxychloride.

The production of aliphatic phosphates such as trialkyl phosphate and trialkoxyalkyl phosphates are generally done in batch processes on a relatively small scale. The production of tributyl phosphate and tributoxyethyl phosphate esters are described in detail in U.S. Pat. No. 3,020,303.

The time lost between batches in batch processes make them time inefficient. Exothermic batch phosphorylation reactions can be made more time efficient by increasing available cooling capacity. This makes it possible to use higher feed rates, shorter reaction cycles and large batch sizes.

Inevitable variations occur in batch size and quality. Low quality is reflected in losses of 6 to 10% which are uneconomical to dispose of under current environmental protection laws.

According to the present invention, there is provided a continuous process for producting aliphatic phosphates in a non-oxidizing atmosphere which comprises:

a. continuously introducing a 20 to 30 weight percent solution of an alkali metal alkoxide into a reactor at a rate of 2 to 30 gallons per minute;

b. continuously introducing phosphorus oxychloride into the reactor under ratio control;

c. reacting the alkali metal alkoxide with the phosphorus oxychloride while maintaining the reaction mixture at 40° C. to 60° C.;

d. continuously controlling the reaction yield;

e. continuously removing reaction products from the reactor; and f. washing the crude phosphate reaction product with water to stop the reaction and remove sodium chloride.

The present continuous process avoids the time inefficiencies of the batch phosphorylation porcesses. Losses are reduced to only 2-3%, typically 2 to 2.5% compared to 6 to 10% losses in batch phosphorylation operations. Surprisingly, the overall efficiency of the present process is improved over the batch process by more than would be expected from reduced down-time.

There are inherent batch to batch variations when conducting batch phosphorylation reactions. An excess of phosphorus oxychloride in the phosphorylation reaction results in producing so-called partial esters which contain some sodium substitution which make the partial esters water soluble. These partial esters are lost when the trialkyl phosphate ester product is washed with water to remove salt. Excess alkoxide is converted to the starting alcohol thus reducing yield and producing a by-product which must be recovered. Small batch reactions, of a few hundred gallons size, vary somewhat in yield from batch to batch due to difficulty in accurately controlling the yield or end point; product yields, before product recovery and refining, of about 80% to 95% have been reported. Commercial batch operations of 5000 gallons or more are difficult to control due to difficulties in maintaining uniform reactant quality. Continuous control of the reaction yield in the present process assures a high uniform yield of 90% to 92% after product recovery and refining.

The alkali metal alkoxide is preferably fed to the reactor as a 28% to 30% solution in a carrier alcohol which is the alcohol from which the alkali metal alkoxide was produced. That is, for sodium butoxide, the carrier alcohol would be butyl alcohol and for sodium 2-butoxyethoxide the alcohol would be 2-butoxyethanol. Other alkoxides useful in practicing the process can be made from 2-ethylhexanol, octanol, N-dodecanol and octadecanol, and from other carbonols such as 2-ethoxyethanol, 2-propoxyethanol and 2-ethoxyethanol.

The alkoxide concentration can vary between about 20 to about 30 weight percent in the carrier alcohol. Higher concentrations of alkoxide in the carrier alcohol can be used but will produce high viscosity reaction mixtures which create problems in mixing and in the downstream handling of the reaction product. Lower alkoxide concentrations pose no problem but when they are used, the capacity of downstream recovery equipment must be in creased. Alkali metal alkoxides of sodium potassium and lithium are employed; sodium alkoxide is preferred for economic reasons.

Commercial grade phosphorus oxychloride is used in the process and nickel or glass-lined equipment should be used for storing and transporting the phosphorus oxychloride to the reactor.

The phosphorylation operation is dependent upon maintaining the temperature in the reactor between about 40° C. and about 60° C. The reaction is exothermic; when the reactor temperature is set for example at 50° C., the actual measured temperature can vary between 45°-55° C. The reaction can be run at temperatures of 40° C. and lower, but at these lower temperatures the high viscosity reaction mixtures require the use of positive displacement pumps, such as gear pumps, in place of conventionally used centrifugal pumps. Operating the reactor at a set point of about 50° C. is convenient because at this temperature the crude product is easily pumped and side reactions are minimal.

Reactor design is not critical to the process but some mixing of the reactants is necessary. Mixing can be effected by means of an agitator in the reactor, mixing nozzles, static mixers and the like.

Temperature control in a stirred tank reactor is accomplished by continually removing a portion of the crude product from the reactor and recirculating it through coolers and back to the reactor. Analytical control of the reaction is conveniently maintained by sampling or measuring properties of this recirculating crude product stream. Changing the phosphorus oxychloride addition ratio also can affect the temperature since the reaction is exothermic. Higher reactant feed rates raise the temperature in the reactor while lower reactant feed rates help to reduce the temperature.

The normal feed rates of the reactants are arranged so that they are fed to the reactor in about a stoichiometric ratio. The crude product is continuously monitored for the presence of an excess of either reactant and the feed rates adjusted to approach as near as possible complete reaction. Continuously monitoring the reaction can be done by automatic sampling and analytical devices, measuring capatance, pH, conductivity or routine analysis.

In making tributyl phosphate, a 30% solution of sodium butoxide in butanol can be fed at a rate of 2-20 gallons per minute or more in a commercial plant.

When using a sodium butoxide feed rate of about 8 to about 11 gallons per minute, the phosphorus oxychloride feed is ratioed from the alkoxide flow and typically ranges from about 450 to about 700 pounds per hour in this operation mode. Under these conditions the process will provide a crude phosphate ester strength of 18-26% tris(butoxyethyl) phosphate or 19-22.5% tributyl phosphate with by-product production of less than 6% based on washing losses. The by-products are typically highly water-soluble partial esters.

The reaction is conducted in a nonoxidizing atmosphere, for example in methane. To avoid the dangers of methane explosions, it is preferred to use inert gases such as nitrogen, carbon dioxide and the like.

The present process will be described with reference to the figure and the manufacture of tributyl phosphate. Sodium butoxide is removed from vessel T-1 by pump P-1and fed through line L-1 to the cooler H-1 where the temperature of the butoxide, if it is hot, is cooled to at least 50° C. The sodium butoxide leaves the cooler through line L8 and enters the agitated reactor R1. Phosphorus oxychloride is removed from storage vessel T2 and enters the reactor R1 through L2. Crude reaction product is removed from the reactor R1 by the pump P2 and circulated through line L3 through cooling devices H1 and H2 after which cooled crude product is returned through line L6 to the reactor. A small side stream is removed from line L3 through line L5 and which contains analytical device A1 and an in-line spare analytical device A2. Part of the crude product is continuously removed from line L3 through L4 into a quenching decanter D1 to which water is added to remove sodium chloride and stop the reaction.

The invention is illustrated by the following examples. The equipment configuration in the examples is as shown in the block diagram and the operation is as described below. In the following examples nitrogen was used as the non-oxidizing atmosphere. The first three examples produced tris-butoxyethyl phosphate and Example 4 through 6 produced tributyl phosphate.

EXAMPLE 1

The plant was started up using a sodium 2-butoxyethoxide 30% solution in 2-butoxyethanol at a flow rate of 5.0 gallons per minute and a phosphorus oxychloride flow rate of 331 pounds per hour. The temperature of the incoming sodium alkoxide solution and the recycled crude product solution were adjusted to maintain the reaction temperature at 45° C. At steady state conditions and substantially cooler reaction, the crude product contained 31% by weight tris-butoxyethyl phosphate.

EXAMPLE 2

Example 1 was repeated except that the sodium 2-butoxyethoxide 2-butoxyethanol solution flow rate was maintained at 8.0 gallons per minute and the phosphorus oxychloride flow rate at 481 pounds per hour. The crude product contained 26.0% by weight tri-butoxyethyl phosphate.

EXAMPLE 3

The process of Example 1 was repeated except that the sodium 2-butoxyethoxide solution in 2-butoxyethanol flow rate was maintained at 21.9 gallons per minute, and the phosphorus oxychloride addition rate was maintained at 620 pounds per hour. The tributoxyethyl phosphate in the crude product going to the quencher was 22.3% by weight.

EXAMPLE 4

The plant as described in the figure and examples above was started up using 30% sodium butoxide solution in butanol at a low rate of 5.0 gallons per minute and a phosphorus oxychloride flow rate of 303 pounds per hour. The temperature of the incoming alkoxide and the crude product recycle were such that the reactor temperature was maintained at 45° C. Under steady state conditions the process produced 17.5% by weight tributyl phosphate in the crude reaction mixture going to the quencher decanter.

EXAMPLE 5

Example 4 was repeated with a sodium butoxide flow rate of 20.0 gallons per minute and a phosphorus oxychloride flow rate of 939 pounds per hour. The reaction temperature was maintained at 46° C. The crude product going to the quencher decanter contained 19.3% by weight tributyl phosphate.

EXAMPLE 6

The process of Example 4 was repeated but using a sodium butoxide flow rate of 13.0 gallons per minute and a phosphorus oxychloride flow rate of 597 pounds per hour. The reactor temperature was maintained at 49° C. The crude product flowing to the quencher decanter contained 17.4% by weight tributyl phospahte.

EXAMPLE 7

The process as practiced in Example 3 was repeated over an extended period. When running continuously under steady-state conditions and continuously controlling the reaction yield over one four day period 146,646 pounds of sodium 2-butoxyethoxide in solution in 2-butoxyethenol was fed to two phosphorylation reactors. During this run 56049 pounds of phosphorus oxychloride was consumed in producing the product tributoxyethyl phosphate in one of the reactors. Based on the alkoxide feed of 146,646 the theoretical amount of phosphorus oxychloride is 53,595 pounds [(146,646/3.140)153.5]. The percent yield based on phosphorus oxychloride=(93,595/56049)×100=95.6%. The overall alcohol yields were influenced by the parallel unit which was operating poorly. The alcohol yields were about 86.4% for the combined units. The alkoxide reactor feeding one phosphosylation reactor was malfunctioning during this run and consumed 36,525 pound of phosphorus oxychloride for an yield based on phsophouus oxychloride of 121.3% which is not possible. This was due to the presence of "wet alkoxide", in which there is free sodium hydroxide in the alkoxide which reacts with the phosphorus oxychloride to produce partial esters where sodium replaces some of the alcohol. This results in low overall yields based on alcohol for the two phosphorylation reactors.

EXAMPLE 8

The process as practiced in Example 5 was repeated over an extended period. Over a 26 day period 892,699 pounds of butanol was fed to parallel operated phosphorylators as a solution of sodium butoxide in butanol with enough phosphorus oxychloride to produce 1,019,314 pounds of tributyl phosphate. The ratio of alcohol to product is 892,699/1,019,314 or 0.8758. The theoretical alcohol to product ratio is 0.8346. The yield based on alcohol consumption=(0.8346/0.8758)×100=95.3%.

We claim:

1. A continuous process for producing aliphatic phosphates in a non-oxidizing atmosphere characterized by:
   a. continuously introducing a 20 to 30 weight percent solution of an alkali metal alkoxide into a reactor at a rate of 2 to 30 gallons per minute;
   b. continuously introducing phosphorus oxychloride into the reaction zone under ratio control;
   c. reacting the alkali metal alkoxide with the phosphorus oxychloride while maintaining the reaction mixture at 40° C. to 60° C.;
   d. continuously controlling the reaction yield;
   e. continuously removing reaction products from the reactor; and
   f. washing the crude phosphate reaction product with water to stop the reaction and remove sodium chloride.

2. The process of claim 1 characterized in that the reaction mixture temperature is maintained between 45° C. and 55° C.

3. The process of claim 1 or 2 characterized in that the alkali metal alkoxide is a temperature of 50° C. or less when added to the reactor.

4. The process of claim 1 characterized in that the alkali metal hydroxide is fed to the reactor as a 28 to 30% solution by weight in the alcohol from which the alkali metal alkoxide was prepared.

* * * * *